United States Patent
Leibowitz

(12) 
(10) Patent No.: US 6,749,859 B2
(45) Date of Patent: Jun. 15, 2004

(54) TOPICAL COMPOSITIONS AND GLOVE FOR PROTECTION AGAINST RADIATION EXPOSURE

(76) Inventor: Jonathan S. Leibowitz, 1470 E. 4th St., 2nd floor, Brooklyn, NY (US) 11230

( * ) Notice: Subject to any disclaimer, the term of this patent is extended or adjusted under 35 U.S.C. 154(b) by 57 days.

(21) Appl. No.: 10/183,118

(22) Filed: Jun. 26, 2002

(65) Prior Publication Data

US 2004/0001894 A1 Jan. 1, 2004

(51) Int. Cl.[7] .......................... H01N 25/34; G21F 3/02
(52) U.S. Cl. ........................ 424/402; 2/16; 2/159; 2/161.7; 250/515.1; 250/516.1
(58) Field of Search ................. 424/402; 2/16, 2/159, 161.7; 250/515.1, 516.1

(56) References Cited

U.S. PATENT DOCUMENTS

| | | | |
|---|---|---|---|
| 5,638,545 A | | 6/1997 | Rosner |
| 5,725,875 A | * | 3/1998 | Noll et al. ............... 424/445 |
| 5,817,325 A | * | 10/1998 | Sawan et al. ........... 424/411 |

* cited by examiner

*Primary Examiner*—James M. Spear
*Assistant Examiner*—Sharon Howard

(57) ABSTRACT

This invention relates to topical compositions and a glove for protection against radiation exposure, such as that due to radiation used in medical procedures.

19 Claims, 2 Drawing Sheets

Cross Section of Double Layer Radiopaque Glove (10)

TOPICAL COMPOSITIONS AND GLOVE FOR PROTECTION AGAINST RADIATION EXPOSURE

FIELD OF THE INVENTION

This invention relates to topical compositions and a glove for protection against radiation exposure, such as that due to radiation used in medical procedures.

BACKGROUND OF THE INVENTION

Over the past several decades there has been a proliferation of medical diagnostic and treatment devices that involve the use of x-rays, beta rays, gamma rays and radioactive isotopes. In addition, there has been recent concern regarding possible radiation exposure from nuclear weapons and terrorist attacks on nuclear facilities.

In the medical field, the use of x-ray fluoroscopy in diagnostic and therapeutic applications has been increasing due to the growth of Interventional Cardiology and Radiology. With this growth, there is an increasing number of medical professionals, including doctors, nurses and technicians (as well as patients), are engaged in its use and thus exposed to its inherent hazard, radiation. There is growing utilization of both beta and gamma rays for the diagnosis and treatment of disease.

Despite various precautions, including monitoring and protective devices (such as lead aprons, gowns, collars, eyeglasses, and gloves), there exist ample occasion and unprotected body area for unwanted radiation exposure. Protective devices frequently are not worn due to their weight, hindrance of dexterity, lack of touch sensation, and unmanageable awkwardness. Some areas of the body, notably the face, are nearly impossible to protect without wearing a cumbersome helmet.

U.S. Pat. No. 5,638,545 discloses an insert for a surgical glove having a flexible, generally planar member which includes a material that attenuates x-rays or other ionizing radiation.

Thus, there is a need for devices which can protect area of the body which may be exposed to damaging radiation without hindering the user's dexterity or loss of touch sensation.

SUMMARY OF THE INVENTION

According to one aspect of the present invention, a topical composition is provided comprising at least one radio-opaque agent and a carrier. The topical composition may be in any form including, but not limited to, a lotion, cream, gel, powder, emulsion, or solution. The topical composition of the present invention can be applied to a surface, such as all or part of a human body, to prevent or reduce exposure to radiation.

Another embodiment of the present invention is a glove which includes a gel, cream, lotion, solution, emulsion, or powder comprising at least one radio-opaque agent. Preferably, the gel, cream, lotion, solution, emulsion, or powder is the topical composition of the present invention. For example, the gel, cream, lotion, solution, emulsion or powder may be disposed within one or more sealed compartments which are integrated into the glove so that it does not contact the user's hand when the glove is worn. According to one preferred embodiment, the glove includes one or more sealed compartments containing a radio-opaque agent which cover the outer dorsal layer of a user's hand (i.e., the side of the hand opposite the palm side) but not the fingers of the hand. According to another preferred embodiment, the glove includes one or more sealed compartments containing a radio-opaque agent which cover the entire outer dorsal layer (including fingers) of a user's hand.

Alternatively, the radio-opaque agent may be coated on the outer and/or inner surface of the glove. When the radio-opaque agent is coated on the inner surface of the glove, the radio-opaque agent may be transferred to the user's hand when the glove is worn by the user.

Yet another embodiment is a glove having at least two separate compartments for the fingers of a user. The glove comprises an outer dorsal layer and a palmer layer. The outer dorsal layer includes a top layer and a bottom layer. At least one radio-opaque agent is disposed between the top and bottom layers. The radio-opaque agent is included in at least the portion of the outer dorsal layer which covers the separate compartments for the fingers of the user.

The glove of the present invention may be worn to prevent or reduce exposure of the hand of a person while maintaining the person's manual dexterity and sense of touch.

DETAILED DESCRIPTION OF THE INVENTION

Figure 1:
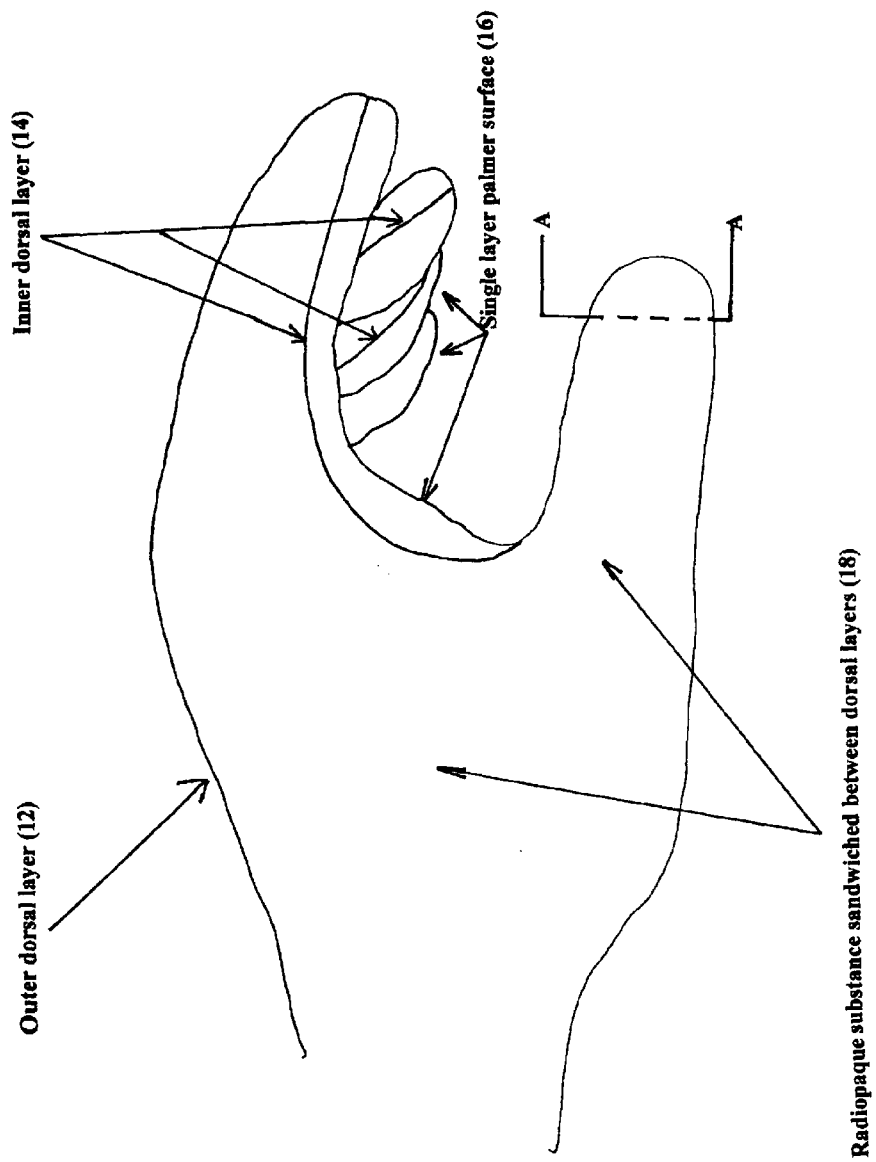
FIG. 1 is an illustration of one embodiment of the glove of the present invention.

The term "radio-opaque agent" refers to any substance or agent which blocks, absorbs, scatters, or reflects any radiation outside the visible light spectrum, including, but not limited to, X-rays (in the wavelength range of 0.01 to 10 nm), beta rays (e.g., having velocities of about 35,000 to 180,000 miles per second), gamma rays (having an energy in the range of $10^4$ to $10^7$ eV), radiation used in radiation therapy (e.g., therapy to treat cancer), and other harmful radiation (such as that resulting from nuclear disasters and nuclear weapons). Suitable radio-opaque agents include, but are not limited to, those comprising platinum, gold, silver, bismuth, mercury, lead, barium, calcium, zinc, aluminum, iron, gallium, iodine, tungsten, and any combination of any of the foregoing. Other suitable radio-opaque agents include, but are not limited to, those commercially available as radio-opaque agents for medical uses, such as ionic and nonionic intravenous radiocontrast agents, diagnostic barium and gastrographin preparations, and gallium preparations.

According to one preferred embodiment, the radio-opaque agent blocks, absorbs, scatters, or reflects any radiation outside the visible light spectrum, including, but not limited to, X-rays, beta rays, and gamma rays, which are emitted from radioisotopes, such as those used in the medical industry (e.g., in radiation therapy and medical diagnostic testing). Examples of radioisotopes used in the medical industry include, but are not limited to, radioisotopes of gallium, iodine, indium, thallium, $^3$H, $^{11}$C, $^{14}$C, $^{13}$N, $^{18}$F, $^{22}$Na, $^{24}$Na, $^{31}$Si, $^{32}$P, $^{35}$S, $^{36}$Cl, $^{38}$Cl, $^{42}$K, $^{45}$Ca, $^{51}$Cr, $^{52}$Mn, $^{54}$Mn, $^{55}$Fe, $^{59}$Fe, $^{60}$Co, $^{63}$Zn, $^{65}$Zn, $^{82}$Br, $^{85}$K, $^{85}$Kr, $^{89}$Sr, $^{99}$Tc, $^{131}$I, $^{137}$Cs, $^{182}$Ta, $^{192}$Ir, and $^{198}$Au.

The term "carrier" includes, but is not limited to, pharmaceutically acceptable carriers, such as water, celluloses (including, but not limited to, methylcellulose).

Topical Composition

The topical composition generally includes an amount of the radio-opaque agent effective to prevent or reduce (e.g., by 10, 20, 30, 40, 50, 60, 70, 80, 90, 95, 99, 99.9, or 99.99%) radiation exposure of a surface to which it is applied. Preferably, the amount is effective to prevent or reduce X-ray, beta ray, and/or gamma ray exposure. This amount may vary depending on the radio-opaque agent incorporated in the topical composition. Preferably, the radio-opaque agent is uniformly dispersed throughout the topical composition. A thickener may be incorporated in the topical composition in order to immobilize or suspend the radio-opaque agent. This prevents the radio-opaque agent from penetrating the user's skin.

The topical composition can also include other excipients known in the art, such as emollients, colorants, and moisturizing agents. Suitable excipients include, but are not limited to, those described in the *Remington's Pharmaceutical Sciences*, 19th Edition, A. R. Gennaro (1995) and the *International Cosmetic Ingredient Dictionary and Handbook*, 7th Edition (1997), published by The Cosmetic, Toiletry, and Fragrance Association (both of which are hereby incorporated by reference).

The topical composition of the present invention is typically applied to a surface in an amount effective to prevent or reduce exposure of the surface (e.g., hands and face) to radiation (such as X-rays, beta rays, and/or gamma rays).

Glove

The glove of the present invention may be composed of latex, cloth, vinyl, or any other substance known in the art. According to one embodiment, the glove is a surgical glove, such as a latex or non-latex glove.

An example of the glove of the present invention is shown in FIG. 1. Glove 10 has an outer dorsal layer 12 and a palmer layer 16 (i.e. on the palm side of the glove). The palmer layer 16 may be comprised of a single layer of material as illustrated in FIG. 1 or may be comprises of multiple layers of the same or different material. The palmer may be composed of a top and bottom layer having a radio-opaque agent disposed between the top and bottom layers. Preferably, the outer dorsal layer 12 and the palmer layer are comprised of the same material.

Figure 2:
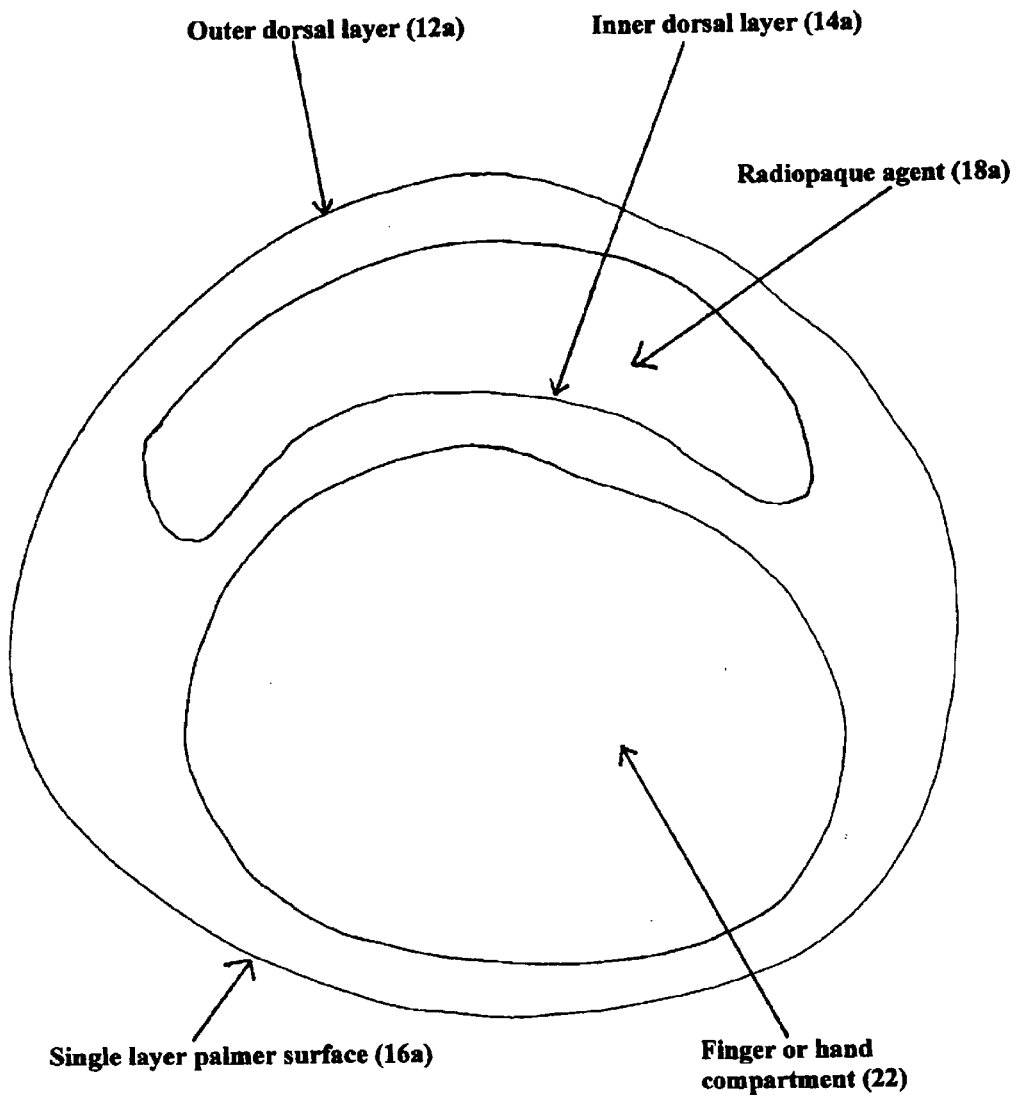
FIG. 2 is a cross-sectional view along lines A—A of FIG. 1.

A cross-section along lines A—A of the glove 10 is shown in FIG. 2. The glove 10 has an inner dorsal layer 14 between the outer dorsal layer 12 (or 12A) and the palmer layer 16 (or 16A). Between the inner dorsal layer 14 and the palmer layer 16 is sufficient space to engage the hand of a person. A compartment 18 disposed between the outer dorsal layer 16 and the inner dorsal layer 14 includes a radio-opaque agent. According to one embodiment, the radio-opaque agent is uniformly dispersed throughout the compartment 18. According to another embodiment, the thickness of the compartment 18 is uniform over the entire inner dorsal layer 14 of the glove 10.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A method for reducing exposure of a surface to radiation comprising the steps of:
    (a) applying a effective amount of a topical composition to the surface, the topical composition comprising at least one radio-opaque agent, and a carrier; and
    (b) exposing the surface to non-naturally occurring radiation selected from X-rays, beta rays, and gamma rays.

2. A method for reducing exposure of all or part of a human body comprising the steps of:
    (a) applying a effective amount of a topical composition to all or part of the body, the topical composition comprising at least one radio-opaque agent, and a carrier; and
    (b) exposing at least part of the body to which the topical composition was applied, to non-naturally occurring radiation selected from X-rays, beta rays, and gamma rays.

3. A method for reducing exposure of hands, face, or both comprising the steps of:
    (a) applying a effective amount of a topical composition to the hands, face, or both, the topical composition comprising at least one radio-opaque agent, and a carrier; and
    (b) exposing the hand, face, or both to which the topical composition was applied, to non-naturally occurring radiation selected from X-rays, beta rays, and gamma rays.

4. A glove comprising a gel, cream, lotion, solution, emulsion, or powder comprising at least one radio-opaque agent, the gel, cream, lotion, solution, emulsion, or powder being on the surface thereof or integrated into the glove.

5. The glove of claim 4, wherein the glove is a surgical glove.

6. The glove of claim 4, wherein the glove is a latex, cloth, or vinyl glove.

7. A glove having comprising:
    (a) an outer dorsal layer having
        (i) a top layer, and
        (ii) a bottom layer,
    wherein at least one radio-opaque agent is disposed between the top and bottom layers; and
    (b) a palmer layer connected to the outer dorsal layer.

8. The glove of claim 7, wherein the palmer surface of at least one finger of the glove is single layered.

9. The glove of claim 8, wherein the palmer surface of all the fingers of the glove are single layered.

10. The glove of claim 8, wherein the entire palmer surface is single layered.

11. The glove of claim 7, wherein the palmer layer has
    (i) a top layer, and
    (ii) a bottom layer,
wherein at least one radio-opaque agent is disposed between the top and bottom layers.

12. A method for reducing exposure of the hand of a person while maintaining manual dextrity and sense of touch, the method comprising the step of applying the glove of claim 7.

13. The method of claim 12, further comprising the step of exposing the glove on the hand of the person to non-naturally occurring radiation selected from X-rays, beta rays, and gamma rays.

14. The method of claim 13, wherein the radiation emanates from a radioisotope.

15. The method of claim 14, wherein the radioisotope is selected from gallium, iodine, indium, thallium, $^{3}H$, $^{11}C$, $^{14}C$, $^{13}N$, $^{18}F$, $^{22}Na$, $^{24}Na$, $^{31}Si$, $^{32}P$, $^{35}S$, $^{36}Cl$, $^{38}Cl$, $^{42}K$, $^{45}Ca$, $^{51}Cr$, $^{52}Mn$, $^{54}Mn$, $^{55}Fe$, $^{59}Fe$, $^{60}Co$, $^{63}Zn$, $^{65}Zn$, $^{82}Br$, $^{85}K$, $^{85}Kr$, $^{89}Sr$, $^{99}Tc$, $^{131}I$, $^{137}Cs$, $^{182}Ta$, $^{192}Ir$, and $^{198}Au$.

16. The method of claim 12, wherein the radio-opaque agent comprises platinum, gold, silver, bismuth, mercury, lead, barium, calcium, zinc. Aluminum, iron, gallium, iodine, tungsten, or a mixture thereof.

17. The method of claim 1, wherein the radiation emanates from a radioisotope.

18. The method of claim 17, wherein the radioisotope is selected from gallium, iodine, indium, thallium, $^3$H, $^{11}$C, $^{14}$C, $^{13}$N, $^{18}$F, $^{22}$Na, $^{24}$Na, $^{31}$Si, $^{32}$P, $^{35}$S, $^{36}$Cl, $^{38}$Cl, $^{42}$K, $^{45}$Ca, $^{51}$Cr, $^{52}$Mn, $^{54}$Mn, $^{55}$Fe, $^{59}$Fe, $^{60}$Co, $^{63}$Zn, $^{65}$Zn, $^{82}$Br, $^{85}$K, $^{85}$Kr, $^{89}$Sr, $^{99}$Tc, $^{131}$I, $^{137}$Cs, $^{182}$Ta, $^{192}$Ir, and $^{198}$Au.

19. The method of claim 1, wherein the radio-opaque agent comprises platinum, gold, silver, bismuth, mercury, lead, barium, calcium, zinc. Aluminum, iron, gallium, iodine, tungsten, or a mixture thereof.

* * * * *

UNITED STATES PATENT AND TRADEMARK OFFICE
CERTIFICATE OF CORRECTION

PATENT NO. : 6,749,859 B2
DATED : June 15, 2004
INVENTOR(S) : Jonathan S. Leibowitz It is certified that error appears in the above-identified patent and that said Letters Patent is hereby corrected as shown below:

Column 3,
Line 65, change "a effective" to -- an effective --

Column 4,
Lines 5 and 15, change "a effective" to -- an effective --
Line 30, delete the word "having"
Line 50, change "dext rity" to -- dexterity --
Line 66, change "zinc. Aluminum" to -- zinc, aluminum --

Column 6,
Line 3, change "zinc. Aluminum" to -- zinc, aluminum --

Signed and Sealed this

Eighth Day of February, 2005

JON W. DUDAS
*Director of the United States Patent and Trademark Office*